(12) United States Patent
Liu et al.

(10) Patent No.: US 7,696,125 B2
(45) Date of Patent: Apr. 13, 2010

(54) CATALYST AND PROCESS FOR PREPARING CARBOXYLIC ACID ESTERS

(75) Inventors: Kindtoken Hwaider Liu, Park Ridge, NJ (US); Man-Yin Lo, Hsinchu (TW); Wen-Chyi Lin, Hsinchu (TW); Mei-Yuan Chang, Hsinchu (TW)

(73) Assignee: Lee Chang Yung Chemical Industry Corporation, Taipei (TW)

( * ) Notice: Subject to any disclaimer, the term of this patent is extended or adjusted under 35 U.S.C. 154(b) by 1290 days.

(21) Appl. No.: 11/174,593

(22) Filed: Jul. 6, 2005

(65) Prior Publication Data

US 2007/0010684 A1 Jan. 11, 2007

(51) Int. Cl.
*C07C 67/44* (2006.01)
*B01J 21/06* (2006.01)

(52) U.S. Cl. ............... 502/258; 560/96; 560/238
(58) Field of Classification Search ............ 560/96, 560/238; 502/258
See application file for complete search history.

(56) References Cited

U.S. PATENT DOCUMENTS 3,855,307 A * 12/1974 Rony et al. ............... 568/454

6,387,841 B1 * 5/2002 Devlin et al. ............... 502/208

FOREIGN PATENT DOCUMENTS

| GB | 1 235 632 | 6/1971 |
| GB | 1 266 623 | 3/1972 |
| GB | 1 266 624 | 3/1972 |
| JP | 57-50545 A | 3/1982 |
| JP | 57-35856 B2 | 7/1982 |
| JP | 57-35860 B2 | 7/1982 |
| JP | 61-243044 A | 10/1986 |
| JP | 61-60820 B2 | 12/1986 |
| JP | 62-7902 B2 | 2/1987 |
| JP | 4-72578 B2 | 11/1992 |
| JP | 5-148184 A | 6/1993 |
| JP | 2003-305366 | 10/2003 |

* cited by examiner

*Primary Examiner*—James O Wilson
*Assistant Examiner*—Ebenezer Sackey
(74) *Attorney, Agent, or Firm*—Muncy, Geissler, Olds & Lowe, PLLC

(57) ABSTRACT

A catalyst and a process for preparing carboxylic acid esters from an aldehyde and an alcohol in the presence of molecular oxygen are disclosed. The catalyst comprises metals supported on a silica-containing support, wherein the metals consist essentially of palladium, lead, an alkali or alkaline earth metal, and at least one of niobium and zirconium. The process for preparing a carboxylic acid ester comprises reacting an aldehyde with an alcohol in the presence of molecular oxygen and the aforementioned catalyst.

10 Claims, No Drawings

CATALYST AND PROCESS FOR PREPARING CARBOXYLIC ACID ESTERS

BACKGROUND

The present invention relates to a catalyst for producing carboxylic acid esters, and more particularly, to a catalyst for producing carboxylic acid esters from aldehydes and alcohols in one-step reaction and a process using such catalyst.

One known process for preparing a carboxylic acid ester from an aldehyde involves first manufacturing a carboxylic acid by oxidizing an aldehyde, and then reacting this carboxylic acid with an alcohol. This process, however, has disadvantages in that it necessitates large equivalent of starting materials since the process involves two-step (oxidation and esterification) reaction operations. Furthermore, the process suffers from poor performance of the catalyst used in the reactions, and the yield of obtained carboxylic acid ester is inadequate.

Several methods have been disclosed with regard to producing high yield carboxylic acid esters in a one-step liquid phase reaction from an aldehyde and an alcohol in the presence of specific catalysts. For example, JP-B-57-135856 proposes Pd and Pb based catalysts using calcium carbonate as a carrier, JP-B-4-72578 proposes Pb based catalysts using zinc oxide as a carrier, JP-A-57-50545 and JP-A-61-243044 propose various types of Pd/Pb based catalysts, JP-B-61-60820 proposes Pd/Bi based catalysts, JP-B-62-7902 and JP-A-5-148184 propose the catalysts composed of Pd and at least one element selected from Pb and Bi, and, JP-B-57-35860 proposes Pd/Tl/Hg based catalysts.

The processes for preparing carboxylic acid ester using aforementioned catalysts, however, have low reaction rates and undesirable by-products.

Thus, further process improvements for preparing a carboxylic acid ester from aldehydes and alcohols are desirable.

SUMMARY

A catalyst for catalyzing a reaction in the formation of a carboxylic acid ester from an aldehyde and an alcohol in the presence of molecular oxygen is provided. The catalyst comprises metals supported on a silica-containing support, wherein the metals comprise palladium, lead, an alkali or alkaline earth metal, and at least one of niobium and zirconium.

The present invention further provides a process for preparing a carboxylic acid ester. The process comprises reacting an aldehyde with an alcohol in the presence of molecular oxygen and the aforementioned catalyst.

More specifically, the process is provided for preparing a carboxylic acid ester from an aldehyde and an alcohol in the presence of molecular oxygen with a catalyst comprising metals supported on a silica-containing support, wherein the metals consist essentially of palladium, lead, an alkali or alkaline earth metal, and at least one of niobium and zirconium.

DETAILED DESCRIPTION

An embodiment of the catalyst for preparing carboxylic acid esters of the invention is described below. The support employed by the catalyst is an oxide. Preferably, the support can be a silica-containing support, which principally contains silica, such as silica support, alumina-silica support (including high silica-alumina support and low silica-alumina support), silica-alumina-magnesia support, crystalline aluminosilicate support, zeolite, or combinations thereof, silica-containing supports, such as silica gel CARIACT provided by Fuji Silysia Chemical Ltd., is commercially available. Silica is considered to not only serve as a support, but is also of a catalyst component.

The metals, supported on the support, can comprise palladium, lead, an alkali or alkaline earth metal, and at least one of niobium and zirconium and are formed by depositing metals and/or metal compounds thereof on the support.

A palladium compound on the support can be converted to palladium metal by reduction using an organic reducing reagent such as formaldehyde, formic acid, hydrazine, methanol, or combinations thereof. The palladium compound on the support also can be converted to palladium metal by reduction using a reducing gas such as hydrogen or the like with or without dilution.

Furthermore, the catalysts can be prepared by the method as described below.

First, at least one of niobium compound and zirconium compound is dissolved in water, and a silica-containing support is added and immersed in the resulted solution. The mixture is then dried under reduced pressure and calcined at more than 300, preferably 300-800° C., to yield the Nb- and/or Zr-modified silica-containing support. Examples of the niobium compound usable in the present invention include niobium acetate, niobium carbonate, niobium chloride, niobium citrate, niobium nitrate, niobium oxalate, niobium sulfate, niobium tartrate or the like. Examples of the zirconium compound usable in the present invention include zirconium acetate, zirconium carbonate, zirconium chloride, zirconium citrate, zirconium oxynitrate, zirconium oxalate, zirconium sulfate, zirconium tartrate, and the like.

Subsequently, a lead compound and an alkali or alkaline earth metal compound are dissolved in water, and the Nb and/or Zr modified silica-containing support is added and immersed in the above solution. The mixture is then dried under reduced pressure and calcined at higher than 300, preferably 300-800° C., to form a Nb and/or Zr/Pb/ alkali or alkaline earth metal modified silica-containing support. The lead compound usable in the present invention can be lead acetate, lead carbonate, lead chloride, lead citrate, lead nitrate, lead oxalate, lead sulfate, lead tartrate, or combinations thereof. Because of their high solubility, lead acetate and lead nitrate are preferred among them. The alkali or alkaline earth metal compound usable in the present invention may be an organic or inorganic salt, an oxide or a hydroxide of an alkali or an alkaline earth metal such as sodium, potassium, magnesium, or calcium. A soluble compound of alkali or alkaline earth metal, such as acetate, carbonate, chloride, citrate, hydroxide, nitrate, oxalate, sulfate, tartrate of sodium, potassium, magnesium or calcium, or combinations thereof, may be more preferably used as a component material of the alkali or alkaline earth metal compound.

Finally, a palladium compound is dissolved in water forming a solution, and the Nb and/or Zr/Pb/ alkali or alkaline earth metal-modified silica-containing support is added and immersed in the above solution to form a suspension. The suspension is concentrated to form a mixture. The mixture is then reduced and filtered, and the cake obtained is washed with water and dried to give a Nb and/or Zr/Pd/Pb/ alkali or alkaline earth metal/$SiO_2$ catalyst.

The palladium element of the catalyst is present in an amount of 1-15 parts by weight, preferably of 3-12 parts by weight, based on 100 parts by weight of the silica-containing support. The lead element of the catalyst is also present in an amount of 1-15 parts by weight, preferably of 3-12 parts by weight, based on 100 parts by weight of the silica-containing support. The alkali or alkaline earth metal of the catalyst is present in an amount of 0.1-10 parts by weight, preferably of 0.3-6 parts by weight, based on 100 parts by weight of the silica-containing support. At least one of niobium and zirconium is present in an amount of 0.1-15 parts by weight, preferably of 0.5-12 parts by weight, based on 100 parts by weight of the silica-containing support.

A process for preparing a carboxylic acid ester employing the aforementioned catalyst is also disclosed. The process comprises reacting an aldehyde with an alcohol in the presence of molecular oxygen and the catalyst.

The aldehydes serving as a starting material include saturated aldehydes, unsaturated aldehydes, aromatic aldehydes or combinations thereof, such as acetaldehyde, propionaldehyde, isobutyl aldehyde, acrolein, methacrolein, crotonaldehyde, p-tolualdehyde, benzaldehyde, or combinations thereof. Methacrolein, acrolein and mixture thereof are more important among the abovementioned aldehydes, since they can serve as the raw materials in production of methacrylic esters and acrylic esters with high industrial value.

The alcohols serving as another starting material include methanol, ethanol, isopropanol, allyl alcohol, methallyl alcohol, or combinations thereof. Methanol is more important among the listed alcohols as they can serve as the raw material in production of methyl methacrylate (MMA) and methyl acrylate with high industrial value.

The mole ratio between the aldehyde and the alcohol is from 1:100 to 1:1, and preferably from 1:10 to 2:3.

Oxygen, air, or oxygen-enriched air can serve as the source of molecular oxygen and is usually supplied by blowing into the reaction solution. Furthermore, hydrogen peroxide may be allowed to exist as an oxidizer in the reaction solution.

The process can be carried out in the temperature range of 20-110° C., preferably of 50-100° C. The process can be carried out under high pressure, normal pressure, or reduced pressure. A polymerization inhibitor such as hydroquinone, methyl ethyl hydroquinone, or p-methoxyphenol can be optionally added to the reaction solution. Note that the process of reacting the aldehyde with the alcohol can be carried out continuously, semi-continuously or batch wise. Further, the aforementioned reaction can be performed with/without a continuous water-withdrawal process.

In general, the catalyst used in the process gradually decreases in activity as time elapses. The yield of the carboxylic acid ester produced with the catalyst used repeatedly for batch reactions or used for a long time for continuous reactions is greatly reduced. Since it is considered that the decrease of catalytic activity results from the loss of lead during reaction, a desired amount of lead can be added additionally to the reaction solution.

The following examples are intended to illustrate the invention more fully without limiting their scope, since numerous modifications and variations will be apparent to those skilled in this art.

Unless otherwise indicated, all parts and percentages are given by weight for liquids and solids, while for gases compositions are given as mole percent, and flow rates are given in normal cubic meters per hour, i.e., at 0° C. and 760 mm-Hg. The fraction of the reacted methacrolein which is converted to MMA is given as the percent selectivity, as is usual in the art.

The following discloses the source and properties for the reagents used in the embodiments and comparative embodiments of the invention for better understanding.

Niobium Oxalate: $Nb_2(OOC-COO)_5$, from NOAH.

Zirconium oxynitrate: $ZrO(NO_3)_2 \cdot 2H_2O$, from SHOWA, 99% purity.

Lead acetate: $Pb(CH_3COO)_2 \cdot 3H_2O$, from SHOWA, 99.5% purity.

Magnesium acetate: $Mg(CH_3COO)_2 \cdot 4H_2O$, from SHOWA, 98% purity.

$PdCl_2$: from ISHIFUKU, 99% purity.

De-ionized $H_2O$.

Silica support: Fuji Silysia CARIACT Q-10, particle size 62-105 #.

Process of Preparing Catalysts

EXAMPLE 1

A Nb-Modified Oxyesterification Catalyst 11.08 g niobium oxalate was added into 170 g de-ionized water. After dissolving, 50 g silica support was added into the above solution to form a mixture 1A. The mixture 1A was then dried under reduced pressure and calcined to give a Nb-modified silica support.

4.33 g of lead acetate and 8.28 g of magnesium acetate were added into 141 g de-ionized water. After dissolving, 47.43 g of the Nb-modified silica support was added into the above solution to form a mixture 1B. The mixture 1B was dried under reduced pressure and then calcined to give a Nb/Pb/Mg-modified silica support.

4.16 g of $PdCl_2$ was added into 199.4 g de-ionized water. After dissolving, 49.85 g of the Nb/Pb/Mg-modified silica support was added into the above solution and the suspension obtained was concentrated to form a dark brown mixture 1C. The mixture 1C was then reduced and filtered, and the cake obtained was washed by de-ionized water and dried to give a black catalyst A comprising Pd/Pb/Nb/Mg supported on the silica support.

The catalyst A contained 5 wt % of Pd, 5 wt % of Pb, 6.58 wt % of Nb and 2 wt % of Mg, based on 100% of silica support.

EXAMPLE 2

A Zr-Modified Oxyesterification Catalyst 18.99 g zirconium oxynitrate was added into 350 g de-ionized water. After dissolving, 100 g silica support was added into the above solution to form a mixture 2A. The mixture 2A was then dried under reduced pressure and calcined to give a Zr-modified silica support.

8.07 g of lead acetate and 15.52 g of magnesium acetate were added into 363.4 g de-ionized water. After dissolving, 87.71 g of the Zr-modified silica support was added into the above solution to form a mixture 2B. The mixture 2B was dried under reduced pressure and then calcined to give a Zr/Pb/Mg-modified silica support.

7.93 g of $PdCl_2$ was added into 382.3 g de-ionized water. After dissolving, 105.96 g of the Zr/Pb/Mg-modified silica support was added into the above solution and the suspension obtained was concentrated to form a dark brown mixture 2C. The mixture 2C was then reduced and filtered, and the cake obtained was washed by de-ionized water and dried to give a black catalyst B comprising Pd/Pb/Zr/Mg supported on the silica support.

The catalyst B contained 5 wt % of Pd, 5 wt % of Pb, 6.45 wt % of Zr and 2 wt % of Mg, based on 100 wt % of silica support.

COMPARATIVE EXAMPLE 1

4.80 g of lead acetate and 9.17 g of magnesium acetate were added into 156.4 g de-ionized water. After dissolving, 55.15 g of silica support was added into the above solution to form a mixture 3A. The mixture 3A was dried under reduced pressure and then calcined to give a Pb/Mg-modified silica support.

4.57 g of $PdCl_2$ was added into 220.4 g de-ionized water. After dissolving, 55.1 g of the Pb/Mg-modified silica support was added into the above solution and the suspension obtained was concentrated to form a dark brown mixture 3B. The mixture 3B was then reduced and filtered, and the cake obtained was washed by de-ionized water and dried to give a catalyst C comprising Pd/Pb/Mg supported on the silica support.

The catalyst C contained 5 wt % of Pd, 5 wt % of Pb, and 2 wt % of Mg, based on 100 wt % of silica support.

Process of Preparing Carboxylic Acid Esters

EXAMPLE 3

The catalyst A of Example 1 was tested at 80° C. under 5 $Kg/cm^2$ pressure in an autoclave equipped with an agitator.

Methacrolein (TCI reagent grade, supplied by Tokyo Kasei Kogyo Co., Ltd.), methanol (Merck, 99.5% purity) and air were mixed to serve as reaction solution feed containing 30% methacrolein in methanol. Furthermore, lead acetate (SHOWA, 99.5% purity) was added to the reaction solution as catalyst stabilizer. The outlet oxygen content controlled at 2-4%. The mole ratio between the aldehyde and the alcohol in the reaction solution was 7:3, and the Pb concentration of the reaction solution was 60 ppm.

When the reaction solution was reacted with 20.5 g of the catalyst A under an introduced air flow, the reaction pressure was raised to 5 Kg/cm$^2$ and the temperature was raised to 80° C.

After feeding additional reaction solution, the feeding rate was raised to 40 ml/h. The liquid products were collected per hour and analyzed by GC, and the gaseous products were analyzed by on-line GC.

The above reaction was carried out in a continuous stirring tank reactor system, and the methacrolein conversion, and selectivity and yield of methyl methacrylate after 10 hours on stream are shown in Table 1.

EXAMPLE 4

Example 4 was carried out in a manner the same as Example 3 excepting for substitution of catalyst B for catalyst A. The methacrolein conversion, and selectivity and yield of methyl methacrylate after 10 hours on stream are shown in Table 1.

COMPARATIVE EXAMPLE 2

Comparative Example 2 was carried out in a manner the same as Example 3 excepting for substitution of catalyst C for catalyst A. The methacrolein conversion, and selectivity and yield of methyl methacrylate after 10 hours on stream are shown in Table 1.

EXAMPLE 5

Example 5 was carried out in a manner the same as Example 4 excepting for with continuous water-withdrawal during reaction. The methacrolein conversion, and selectivity and yield of methyl methacrylate after 50 hours on stream are shown in Table 1.

TABLE 1

Oxyesterification of methacrolein with methanol

| Example | Catalyst | Component of Catalyst (%) | | | | | | Methacrolein Conversion (%) | Selectivity (%) | Yield (%) |
| --- | --- | --- | --- | --- | --- | --- | --- | --- | --- | --- |
| | | Nb | Zr | Pd | Pb | Mg | SiO$_2$ | | | |
| Example 3 | Catalyst A | 6.58 | | 5 | 5 | 2 | 100 | 67.0 | 68.4 | 45.8 |
| Example 4 | Catalyst B | | 6.45 | 5 | 5 | 2 | 100 | 67.5 | 67.2 | 45.4 |
| Comparative Example 2 | Catalyst C | | | 5 | 5 | 2 | 100 | 58.3 | 58.7 | 34.2 |
| Example 5 | Catalyst B | | 6.45 | 5 | 5 | 2 | 100 | 72.5 | 92.8 | 67.3 |

EXAMPLE 6

Example 6 was carried out in a manner the same as Example 4 except that ethanol (Nihon Shiyaku Industries, 99.5% purity) was used instead of methanol, and that the feed solution contained 15% methacrolein in ethanol instead of 30% methacrolein in methanol. The methacrolein conversion, and selectivity and yield of ethyl methacrylate after 10 hours on stream are shown in Table 2.

COMPARATIVE EXAMPLE 3

Comparative Example 3 was carried out in a manner the same as Example 6 excepting for substitution of catalyst C for catalyst B. The methacrolein conversion, and selectivity and yield of ethyl methacrylate after 10 hours on stream are shown in Table 2.

TABLE 2

Oxyesterification of methacrolein with ethanol

| Example | Catalyst | Catalyst Components (wt %) | | | | | | Methacrolein Conversion (%) | Selectivity (%) | Yield (%) |
| --- | --- | --- | --- | --- | --- | --- | --- | --- | --- | --- |
| | | Nb | Zr | Pd | Pb | Mg | SiO$_2$ | | | |
| Example 6 | Catalyst B | | 6.45 | 5 | 5 | 2 | 100 | 42.9 | 68.6 | 29.4 |
| Comparative Example 3 | catalyst C | | | 5 | 5 | 2 | 100 | 35.3 | 69.8 | 24.6 |

While the invention has been described by way of examples and in terms of preferred embodiments, it is to be understood that the invention is not limited thereto. It is therefore intended that the following claims be interpreted as covering all such alteration and modifications as fall within the true spirit and scope of the invention.

What is claimed is:

1. A catalyst for catalyzing a reaction in the formation of a carboxylic acid ester from an aldehyde and an alcohol in the presence of molecular oxygen, comprising metals supported on a silica-containing support, wherein the metals comprise palladium, lead, an alkali or alkaline earth metal, and at least one of niobium and zirconium.

2. The catalyst as claimed in claim 1, wherein each of the palladium and lead elements is present in an amount of 1-15 parts by weight, based on 100 parts by weight of the silica-containing support.

3. The catalyst as claimed in claim 1, wherein the alkali or alkaline earth metal is present in an amount of 0.1-10 parts by weight, based on 100 parts by weight of the silica-containing support.

4. The catalyst as claimed in claim 1, wherein at least one of niobium and zirconium is present in an amount of 0.1-15 parts by weight, based on 100 parts by weight of the silica-containing support.

5. The catalyst as claimed in claim 1, wherein each of the palladium and lead elements is present in an amount of 3-12 parts by weight, based on 100 parts by weight of the silica-containing support.

6. The catalyst as claimed in claim 1, wherein the alkali or alkaline earth metal is present in an amount of 0.3-6 parts by weight, based on 100 parts by weight of the silica-containing support.

7. The catalyst as claimed in claim 1, wherein at least one of niobium and zirconium is present in an amount of 0.5-12 parts by weight, based on 100 parts by weight of the silica-containing support.

8. The catalyst as claimed in claim 1, wherein the alkali or alkaline earth metal is magnesium.

9. The catalyst as claimed in claim 1, wherein the metals supported on the silica-containing support consisting essentially of palladium, lead, an alkali or alkaline earth metal, and niobium.

10. The catalyst as claimed in claim 1, wherein the metals supported on the silica-containing support consisting essentially of palladium, lead, an alkali or alkaline earth metal, and zirconium.

* * * * *